(12) United States Patent
Chien

(10) Patent No.: US 9,891,348 B2
(45) Date of Patent: Feb. 13, 2018

(54) CONTACT LENS MATERIAL AND CONTACT LENS

(71) Applicant: HON HAI PRECISION INDUSTRY CO., LTD., New Taipei (TW)

(72) Inventor: Hsiu-Wen Chien, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 237 days.

(21) Appl. No.: 14/969,878

(22) Filed: Dec. 15, 2015

(65) Prior Publication Data

US 2017/0146694 A1    May 25, 2017

(51) Int. Cl.
| | | |
|---|---|---|
| *B02B 1/04* | (2006.01) | |
| *A61L 27/44* | (2006.01) | |
| *A61L 27/58* | (2006.01) | |
| *G02B 1/04* | (2006.01) | |
| *A61L 27/54* | (2006.01) | |
| *A61L 27/52* | (2006.01) | |
| *A61L 27/48* | (2006.01) | |

(52) U.S. Cl.
CPC ............ *G02B 1/043* (2013.01); *A61L 27/446* (2013.01); *A61L 27/48* (2013.01); *A61L 27/52* (2013.01); *A61L 27/54* (2013.01); *A61L 27/58* (2013.01); *A61L 2300/11* (2013.01); *A61L 2300/404* (2013.01); *A61L 2300/604* (2013.01); *A61L 2300/62* (2013.01); *A61L 2400/12* (2013.01)

(58) Field of Classification Search
CPC ........ A61L 27/446; A61L 27/48; A61L 27/52; A61L 27/54; A61L 27/58; A61L 2300/11; A61L 2300/404; A61L 2300/604; A61L 2300/62; A61L 2400/12; G02B 1/043
USPC .......................................................... 524/591
See application file for complete search history.

(56) References Cited

U.S. PATENT DOCUMENTS

2011/0217355 A1* 9/2011 Chauhan .............. A61K 9/0051
424/429

* cited by examiner

*Primary Examiner* — Ling Choi
*Assistant Examiner* — Chun-Cheng Wang
(74) *Attorney, Agent, or Firm* — ScienBiziP, P.C.

(57) ABSTRACT

A contact lens for the human eye includes a matrix and polymer nanocapsules mixed in the matrix. The polymer nanocapsule is calculated to decompose by chemical reaction and thereby release oxygen, to prevent corneal hypoxia. A material for making a contact lens is also provided.

16 Claims, No Drawings

CONTACT LENS MATERIAL AND CONTACT LENS

CROSS-REFERENCE TO RELATED APPLICATIONS

This application claims priority to Taiwanese Patent Application No. 104139039 filed on Nov. 24, 2015 in the Taiwanese Intellectual Property Office, the contents of which are incorporated by reference herein.

FIELD

The subject matter herein generally relates to optical materials, and contact lens made therewith.

BACKGROUND

Contact lens is often used by people but such use easily leads to corneal hypoxia.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The term "comprising" when utilized, means "including, but not necessarily limited to"; it specifically indicates open-ended inclusion or membership in the so-described combination, group, series and the like.

The present disclosure is described in relation to a contact lens. The contact lens includes a matrix and a polymer nanocapsule mixed in the matrix. The polymer nanocapsule includes a hydrogen peroxide ($H_2O_2$) solution and a wall material configured to receive the hydrogen peroxide solution. The side wall of the wall material is configured to slowly decompose in the matrix to release the hydrogen peroxide solution. The hydrogen peroxide solution decomposes to release oxygen and water to enhance or act as substitute for the oxygen permeability of the contact lens, and to prevent corneal hypoxia. When using the contact lens, the decomposition of the hydrogen peroxide is speeded up by sunlight. Further, a catalyst can be added to the contact lens to speed up the decomposition rate of the hydrogen peroxide. Hydrogen peroxide has a disinfection function, and the provision of a disinfecting function can prevent the infection of the eyes by microorganisms.

In at least one embodiment, the polymer nanocapsule has a mass percentage of about 0.01% to about 5% of a total mass of the contact lens.

The polymer nanocapsule includes a hydrogen peroxide solution and a wall material. The hydrogen peroxide solution has a mass percentage of about 0.05% to about 10% of a total mass of the polymer nanocapsule. The hydrogen peroxide has a mass percentage of about 1% to about 35% of a total mass of the hydrogen peroxide solution. The wall material can be one or more of biodegradable polymer materials, such as chitin, poly lactic-co-glycolic acid (PLGA), sodium alga acid, gelatin, and others.

In at least one embodiment, when the contact lens is a hydrogel lens, the matrix is hydrogel. When the contact lens is a silicone hydrogel lens, the matrix is silicone hydrogel. The hydrogel and the silicone hydrogel are formed of hydrophilic monomers and hydrated polymers which have undergone a polymerization reaction by means of a photoinitiator and a cross-linking agent. The hydrated polymers function as structural frame or skeleton of the hydrogel and the silicone hydrogel. The hydrophilic monomers are bonded to the hydrated polymers to improve hydrophilicity and oxygen permeability of the hydrogel and the silicone hydrogel. Further, the hydrophilic monomers and hydrated polymers have a mass percentage of about 94% to about 99.95% of a total mass of the contact lens. The cross-linking agent has a mass percentage of about 0.001% to about 2% of a total mass of the contact lens. The photoinitiator has a mass percentage of about 0.005% to about 1.5% of a total mass of the contact lens.

When the matrix is hydrogel, the hydrophilic monomers may be selected from a group consisting of N-vinyl pyrrolidone (NVP), glycidyl methacrylate (GMA), and N,N-dimethylacrylamide (DMAA), or any combination thereof. The hydrated polymers may comprise methyl methacrylate (MMA) and 2-hydroxyethyl methacrylate (HEMA). When the matrix is silicone hydrogel, the hydrophilic monomers may be N-vinyl pyrrolidone (NVP). The hydrated polymers may be selected from a group consisting of methyl methacrylate (MMA), 2-hydroxyethyl methacrylate (HEMA), polydimethylsiloxane (PDMS), and tris (hydroxyl methyl) aminomethan. The photoinitiator may be available commercially from Chemical Industries Basel (CIBA) Corporation as a clear liquid under the trade name "Irgacure-1173". The cross-linking agent may be ethylene glycol dimethacrylate (EGDMA).

The present disclosure is also described in relation to manufacture of a contact lens. The material for the contact lens includes polymer nanocapsules, hydrophilic monomers, hydrated polymers, a photoinitiator, and a cross-linking agent. When exposed to light, the hydrophilic monomers and hydrated polymers undergo a polymerization reaction under the function of the photoinitiator and the cross-linking agent to form the matrix, thereby causing the polymer nanocapsules to be dispersed in the matrix. The polymer nanocapsules include the hydrogen peroxide solution.

The embodiments shown and described above are only examples. Many details are often found in the art such as the other features of a contact lens material and contact lens manufacture. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, including in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:
1. A contact lens, comprising:
   a matrix; and a polymer nanocapsule dispersed in the matrix;
wherein the polymer nanocapsule is configured to release the oxygen upon degradation in the matrix.

2. The contact lens of claim 1, wherein the polymer nanocapsule comprises a hydrogen peroxide solution and a wall material configured to receive the hydrogen peroxide solution.

3. The contact lens of claim 2, wherein the polymer nanocapsule has a mass percentage of about 0.01% to about 5% of a total mass of the contact lens.

4. The contact lens of claim 3, wherein the hydrogen peroxide solution has a mass percentage of about 0.05% to about 10% of a total mass of the polymer nanocapsule, and the hydrogen peroxide has a mass percentage of about 1% to about 35% of a total mass of the hydrogen peroxide solution.

5. The contact lens of claim 2, wherein the wall material can be biodegradable polymer materials.

6. The contact lens of claim 5, wherein the wall material can be chitin, poly lactic-co-glycolic acid (PLGA), sodium alga acid, gelatin, and so on.

7. The contact lens of claim 1, wherein the matrix is hydrogel; the hydrophilic monomers are selected from a group consisting of N-vinyl pyrrolidone, glycidyl methacrylate, and N,N-dimethylacrylamide, or any combination thereof; the hydrated polymers comprise methyl methacrylate and 2-hydroxyethyl methacrylate.

8. The contact lens of claim 1, wherein the matrix is silicone hydrogel; the hydrophilic monomers are N-vinyl pyrrolidone; the hydrated polymers are selected from a group consisting of methyl methacrylate, 2-hydroxyethyl methacrylate (HEMA), polydimethylsiloxane (PDMS), and tris hydroxyl methyl aminomethan.

9. A contact lens material for making a contact lens comprising:
a polymer nanocapsule;
hydrophilic monomers;
hydrated polymers;
a photoinitiator; and
a cross-linking agent;
wherein, when exposed to light, the hydrophilic monomers and hydrated polymers undergo a polymerization reaction under a function of the photoinitiator and the cross-linking agent to form a matrix, thereby causing the polymer nanocapsule to be dispersed in the matrix.

10. The contact lens material of claim 9, wherein the polymer nanocapsule comprises a hydrogen peroxide solution and a wall material configured to receive the hydrogen peroxide solution.

11. The contact lens material of claim 10, wherein the polymer nanocapsule has a mass percentage of about 0.01% to about 5% of a total mass of the contact lens.

12. The contact lens material of claim 11, wherein the hydrogen peroxide solution has a mass percentage of about 0.05% to about 10% of a total mass of the polymer nanocapsule, and the hydrogen peroxide has a mass percentage of about 1% to about 35% of a total mass of the hydrogen peroxide solution.

13. The contact lens material of claim 10, wherein the wall material can be biodegradable polymer materials.

14. The contact lens of material claim 13, wherein the wall material can be chitin, poly lactic-co-glycolic acid (PLGA), sodium alga acid, gelatin, and so on.

15. The contact lens of material claim 9, wherein the matrix is hydrogel; the hydrophilic monomers are selected from a group consisting of N-vinyl pyrrolidone, glycidyl methacrylate, and N,N-dimethylacrylamide, or any combination thereof; the hydrated polymers comprise methyl methacrylate and 2-hydroxyethyl methacrylate.

16. The contact lens of material claim 9, wherein the matrix is silicone hydrogel; the hydrophilic monomers are N-vinyl pyrrolidone; the hydrated polymers are selected from a group consisting of methyl methacrylate, 2-hydroxyethyl methacrylate (HEMA), polydimethylsiloxane (PDMS), and tris hydroxyl methyl aminomethan.

* * * * *